United States Patent
Dutu et al.

(10) Patent No.: US 9,724,535 B1
(45) Date of Patent: Aug. 8, 2017

(54) LOW FREQUENCY MAGNETIC PULSE VARIABLE RESONATOR FOR ACTIVELY INFLUENCING THE INTERACTION AND INTERCOMMUNICATION AT THE CELLULAR LEVEL FOR BIOLOGICAL ORGANISMS AND MOLECULAR LEVEL OF MATTER

(71) Applicant: BLUGREEN TECHNOLOGIES, INC., Boca Raton, FL (US)

(72) Inventors: Iulius Dutu, Boca Raton, FL (US); Razvan Dutu, Boca Raton, FL (US)

(73) Assignee: BLUGREEN TECHNOLOGIES, INC., Boca Raton, FL (US)

( * ) Notice: Subject to any disclaimer, the term of this patent is extended or adjusted under 35 U.S.C. 154(b) by 0 days.

(21) Appl. No.: 14/550,176

(22) Filed: Nov. 21, 2014

Related U.S. Application Data (63) Continuation-in-part of application No. 13/957,979, filed on Aug. 2, 2013, now abandoned.

(60) Provisional application No. 61/766,226, filed on Feb. 19, 2013.

(51) Int. Cl.
  *A61N 2/02* (2006.01)
  *A61B 5/01* (2006.01)
  *A61B 5/024* (2006.01)

(52) U.S. Cl.
  CPC ............... *A61N 2/02* (2013.01); *A61B 5/01* (2013.01); *A61B 5/024* (2013.01)

(58) Field of Classification Search
  CPC .............. A61N 1/36014; A61N 1/0484; A61N 1/36021; A61N 1/36139; A61N 1/452; A61N 1/36135; A61N 2/02; A61N 2/008; A61B 5/01; A61B 5/024

USPC .................................................. 600/9, 13–14
  See application file for complete search history.

(56) References Cited

U.S. PATENT DOCUMENTS

| | | | |
|---|---|---|---|
| 4,097,769 A * | 6/1978 | Wilson et al. ............... 327/459 |
| 4,541,432 A * | 9/1985 | Molina-Negro et al. ....... 607/46 |
| 5,030,196 A * | 7/1991 | Inoue ....................... A61N 2/12 |
| | | | 361/143 |
| 6,443,883 B1 * | 9/2002 | Ostrow et al. ................. 600/14 |
| 7,367,935 B2 | 5/2008 | Mechlenburg et al. |
| 7,591,776 B2 | 9/2009 | Phillips et al. |
| 7,601,114 B2 | 10/2009 | Goodwin et al. |
| 7,758,490 B2 | 7/2010 | Pilla et al. |

(Continued)

FOREIGN PATENT DOCUMENTS

WO  WO 2011053607 A1 *  5/2011

OTHER PUBLICATIONS

Hauge et al. ("Characterization of consistent triggers of migraine with aura" Cephalalgia. 2011, vol. 31(4), pp. 416-438).*

(Continued)

*Primary Examiner* — Christine H Matthews
*Assistant Examiner* — Kaylee Wilson
(74) *Attorney, Agent, or Firm* — Daniel S. Polley, P.A.

(57) ABSTRACT

An apparatus and method is provided for healing and regeneration of live human and animal bodies and influencing interaction and intercommunication at the cellular level. The apparatus can include one or more environmental and/or body sensors. An electrical circuit can also be provided to produce a square or trapezoidal wave that is delivered to a transducer for application, preferably timed at specific frequencies Delta, Theta, Alpha, to Beta, based on information received from the one or more sensors.

18 Claims, 12 Drawing Sheets

(56) References Cited

U.S. PATENT DOCUMENTS

| | | | |
|---|---|---|---|
| 7,857,747 | B2 | 12/2010 | Muntermann |
| 7,896,797 | B2 | 3/2011 | Pilla et al. |
| 8,212,554 | B2 | 7/2012 | Brazdeikis et al. |
| 8,216,121 | B2 | 7/2012 | Gleim et al. |
| 8,308,627 | B2 | 11/2012 | Friberg |
| 8,308,628 | B2 | 11/2012 | Creighton |
| 8,357,152 | B2 | 1/2013 | Govari et al. |
| 8,376,925 | B1 | 2/2013 | Dennis et al. |
| 8,430,805 | B2 | 4/2013 | Burnett et al. |
| 8,435,166 | B2 | 5/2013 | Burnett et al. |
| 8,560,075 | B2 | 10/2013 | Covalin |
| 2003/0028072 | A1* | 2/2003 | Fischell ............ A61N 1/32 600/13 |
| 2003/0095022 | A1* | 5/2003 | Boynton ............ A61N 2/02 335/299 |
| 2004/0267333 | A1* | 12/2004 | Kronberg .................. 607/72 |
| 2005/0182287 | A1* | 8/2005 | Becker ............... A61N 2/02 600/13 |
| 2005/0237479 | A1* | 10/2005 | Rose .................. A61N 5/0618 351/123 |
| 2007/0021803 | A1* | 1/2007 | Deem et al. .................. 607/46 |
| 2007/0225769 | A1* | 9/2007 | Smith et al. ................... 607/3 |
| 2010/0042009 | A1* | 2/2010 | Lingg ........................ 600/509 |
| 2010/0057655 | A1* | 3/2010 | Jacobson ............. A61N 2/02 706/45 |
| 2011/0021863 | A1* | 1/2011 | Burnett ............... A61N 2/008 600/14 |
| 2012/0302821 | A1* | 11/2012 | Burnett ............... A61N 2/008 600/14 |

OTHER PUBLICATIONS

Adafruit Industries Website, "BMP085 Barometric Pressure/Temperature/Altitude Sensor—5V ready" accessed online Jul. 22, 2016, avaliable online Oct. 24, 2012 at http://www.adafruit.com/products/391.*

* cited by examiner

LOW FREQUENCY MAGNETIC PULSE VARIABLE RESONATOR FOR ACTIVELY INFLUENCING THE INTERACTION AND INTERCOMMUNICATION AT THE CELLULAR LEVEL FOR BIOLOGICAL ORGANISMS AND MOLECULAR LEVEL OF MATTER

This application is a Continuation-In-Part of U.S. application Ser. No. 13/957,979, filed Oct. 2, 2013, which claims priority to and the benefit of U.S. Application Ser. No. 61/766,226, filed Feb. 19, 2013. Both applications are incorporated by reference in their entirety.

BACKGROUND OF THE DISCLOSURE

Magnetic influence on living bodies has been known for a long time starting from ancient Greece and Egypt and is currently used as a therapeutic technique in different ways, including with permanent magnets to pulse an electromagnetic field. Research into magnetic therapy proves the health benefits in living bodies. As a result the number of people who sleep on magnetic beds and/or who wear magnets during the day is continually increasing. These uses have shown the energy increase on bodies and have achieved success in the healing process.

It turns out that pulse magnetic frequencies appear to act as a whole body battery recharger by pumping and priming the cells of the body. The cells in the body are similar to little wet batteries that operate ideally at around 70 millivolts. The membrane acts like a one-way rectifier that converts the earth's magnetic pulse intro electrical potential energy, which charges the body cells. This energy drives cell metabolism and enhances oxygenation, improves absorption of nutrition and essential elements into the cell and can help to remove waste out of the cell. The entire process of regeneration and healing has used frequencies and energy of the planet Earth, namely the Schumann resonant frequencies and the Earth's magnetic field.

SUMMARY OF THE DISCLOSURE

Disclosed is an apparatus for enhancing regenerative, recovery and healing of a living body. The disclosed embodiments preferably comprise at least one environmental and/or body sensor connected to an electrical circuit, which applies a preferred, but not limiting, trapezoidal or square wave varying electrical current to a transducer at a different frequency to generate an electromagnetic field output.

The disclosed apparatus preferably changes the frequency from Delta, Theta, Alpha to Beta (1 Hz-30 Hz) based on the sensor(s) and will produce an electromagnetic force intensity of about 0.001 to about 0.45 Gauss, continuously forever how long the supplied power is present. The disclosed apparatus preferably can generate a same or highly similar type of energy that exist and is created by planet earth.

Thus, the disclosed embodiments provide for a method and apparatus for regenerative, recovery and healing for live humans and animals by applying a low frequency of an electromagnetic pulse which can be varied based on one or more environmental and/or body conditions and which influence interaction and intercommunication at the cellular level for biological organisms and molecular level of matter.

DETAILED DESCRIPTION

Figure 1:
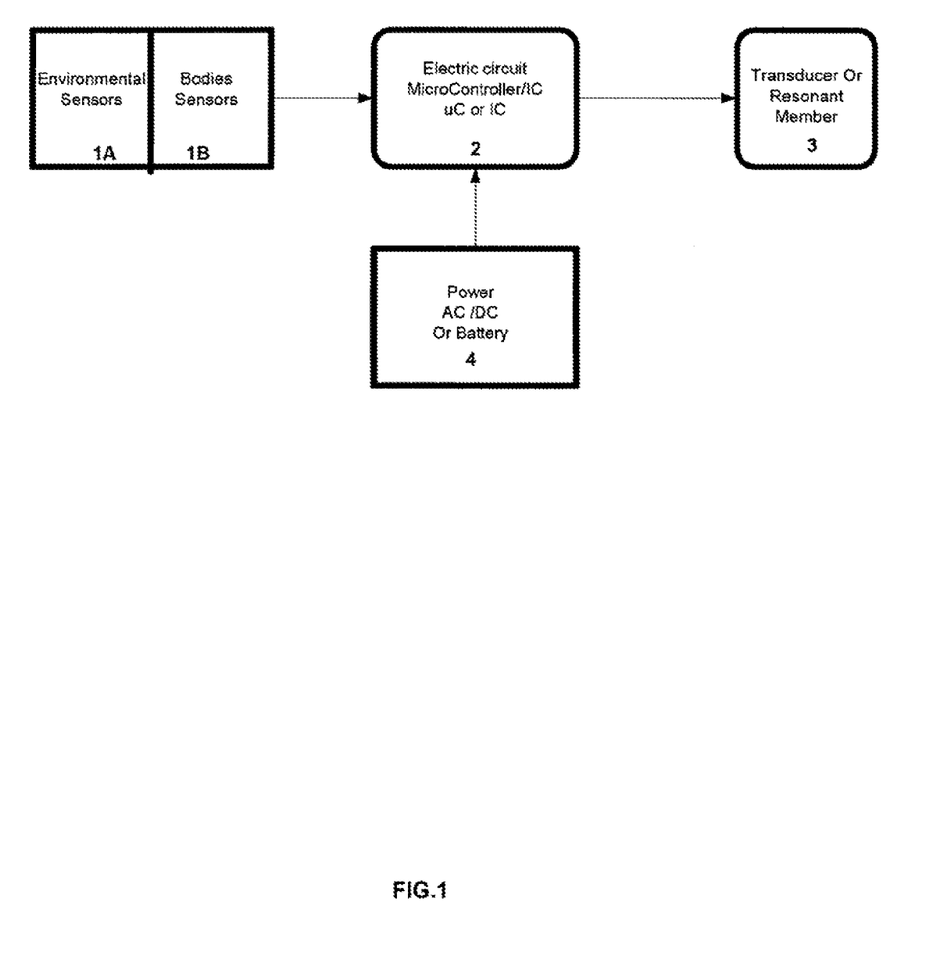
FIG. 1 is a block diagram of the main components for one embodiment of the energy generating apparatus in accordance with the disclosure.

The several embodiments for the disclosed apparatus will be more fully described below, but is not limited by the attached figures and ensuing description in which:

In FIG. 1 blocks 1A and 1B represent the one or more sensors that can be used with the disclosed apparatus, with Block 1A used to denote one or more environmental sensor(s), such as, but not limited to, barometric pressure sensor, temperature sensor, oxygen level sensor, photo sensor, etc. One or more multiple sensors or embodied sensor (such as a MPL115A2 sensor, though not limiting, which in one miniature foot print can read the barometric pressure and temperature) can be used in the apparatus for supplying information which will be used to vary the frequency and/or electromagnetic intensity. Block 1B shows the one or more sensors that can be attached to or located approximate to or near a live body and can read, without limitation, body temperature, heartbeat, pH level, etc.

One or multiple environmental sensors (1A) and/or body sensors (1B) can be in communication with an electrical circuit which is preferably run by a microcontroller or regular integrated circuit ("IC") (block 2). The circuit/microcontroller/IC determines what change to the frequency and/or electromagnetic field intensity has occurred, if any, based on information received from environmental sensor(s) 1a and/or body sensor(s) 1b.

In a more complex embodiment for the apparatus a variety of sensors can be used for providing the information that is used for determining any varying of the frequency and/or the intensity of electromagnetic force. The determination can be based on a programmed algorithm, which will yield the most efficient results for regenerating, balances and healing of a live body. The power (block 4) can be a portable unit with battery(ies) having between about 6 to about 12 volts, and/or a stationary unit using an AC/DC power supply (about 100 to about 240 volt; about 50 Hz to about 60 Hz, to about 6 VDC to about 12 VDC). Block 3 represents the transducer coil which can be used for supplying conductive coil (based on the output from the microcontroller or IC) which preferably can be in a square or trapezoidal wave form, though such is not considered limiting. The transducer or resonator 3 receives the electric pulse or signal from the electrical circuit 2 and provides or creates a magnetic pulse output. Based on information received from sensors 1A and/or 1B the frequency generated by the electrical circuit can be varied and/or changes can be made to the intensity of the magnetic pulse output from transducer or resonator 3.

Alternatively, the electromagnetic force can be generated by a four axis resonate frequency member preferably composed of four conductive coils placed on each side of a trunk pyramid at approximately ⅔ from the base with both bases being open such that a hand or leg can go through. In another embodiment, the coil sizes can be chosen such that they can encompass an entire live human or animal body. The frequency resonator embodiment shown in FIG. 2 can create a resonant frequency that can provide increased healing and regeneration of live human and animal bodies.

Figure 2:
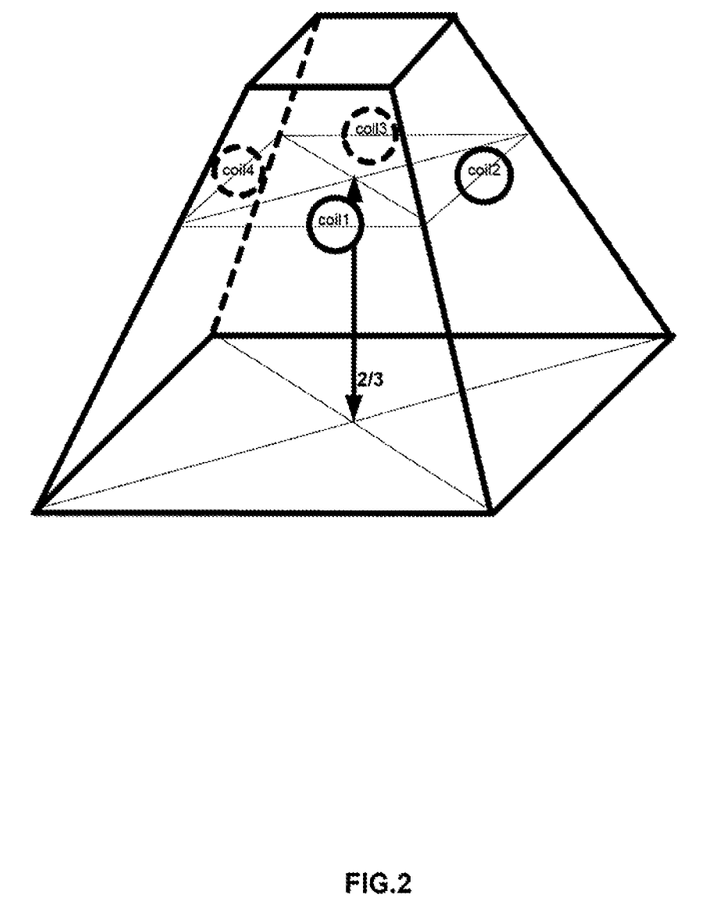
FIG. 2 is an illustration showing one embodiment for the frequency resonator that can be used in accordance with the disclosure.

The frequency resonator shown FIG. 2 can be an electromagnetic resonant assembly preferably compose of four conductive coils connected sequentially to the microcontroller output two sequentially in opposite axis in the same time or all four simultaneous. Other number of conductive coils can also be provided and similarly connected with the microcontroller and are also considered within the scope of the invention.

Figure 3:
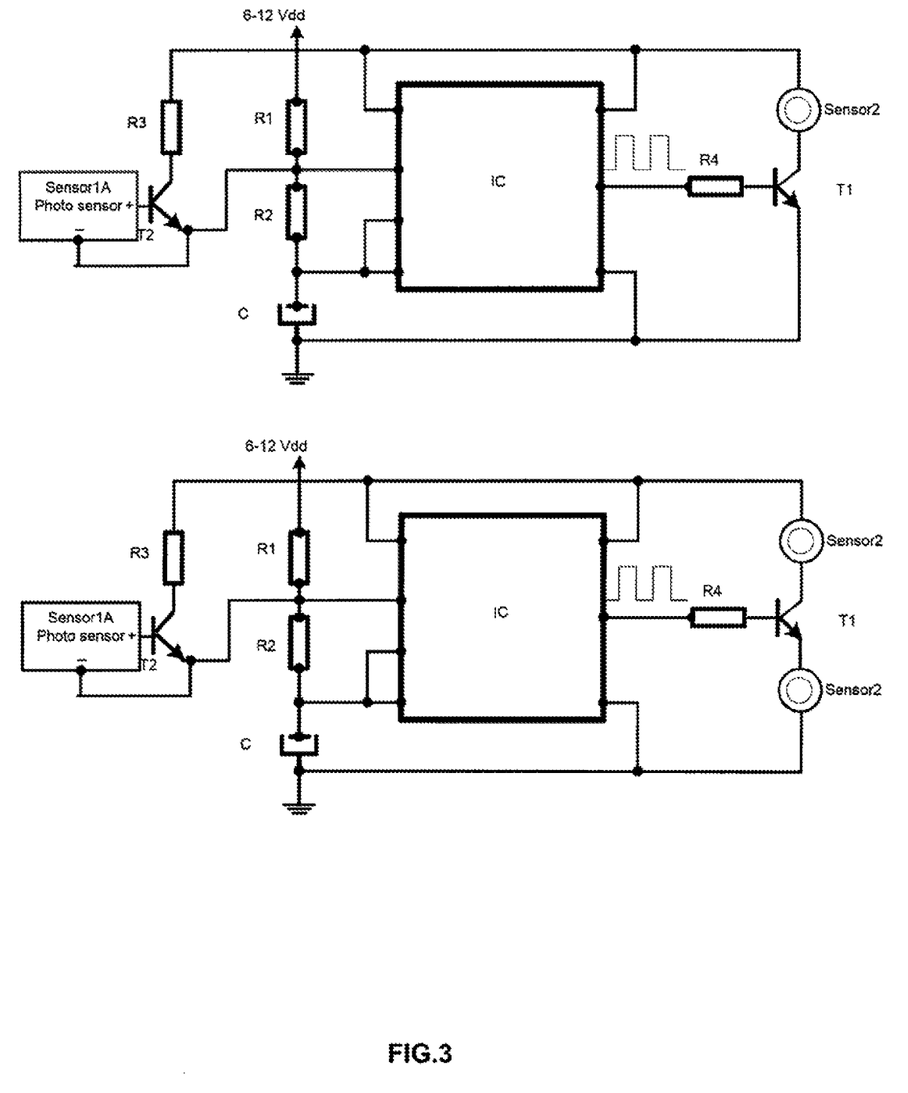
FIG. 3 is an electrical schematic for one embodiment of the disclosed apparatus which is shown using an IC chip and at least one environmental sensor.

As seen in FIG. 3, one embodiment for an electrical circuit of the apparatus is disclosed for healing and regenerating live human and animal bodies and reveals a first novel example for producing an electromagnetic pulse with a varying frequency, the intensity of the magnetic force and alternating the polarity based on information received from a photo sensor. Though a photo sensor has been shown for the electrical circuit, it should be recognized that other sensors, such as, but not limited to, one or more of the above mentioned sensors can also be selected in place or in addition to the photo sensor, and use of such other sensors are also considered within the scope of the disclosure.

In this embodiment, in the presence of light a live body usually is in an active stage (awake stage) and the photo sensor can activate transistor T1 causing resistor R3 to be connected in parallel with resistor R1. With transistor T1 activated, the IC circuit generates a frequency in a high alpha-low beta range (about 11 Hz-about 12.5 Hz). In the absence of light or a low intensity of light the living body is usually in a relaxed stage and the photo sensor will not activate the base of transistor T1. Thus, resistor R3 will not be connected to anything and the IC circuit generates a different frequency of a high theta-low alpha range (about 7.7 Hz-about 8.2 Hz).

The IC circuit can be setup and/or programmed to generate two different frequencies which can alternate at a specific time in order to allow the changing of polarity of the electromagnetic field. Each frequency can be changed by information received from any sensor connected to the IC circuit. The above teaching is not considered limiting and is only one non-limiting example for functionality of the present invention and one non-limiting use/method for the regenerative, healing apparatus. Similarly, the above presentation for the operation of the circuit shown in FIG. 3 is also applicable when other types of sensor(s) are connected to the electric circuit.

Figure 4:
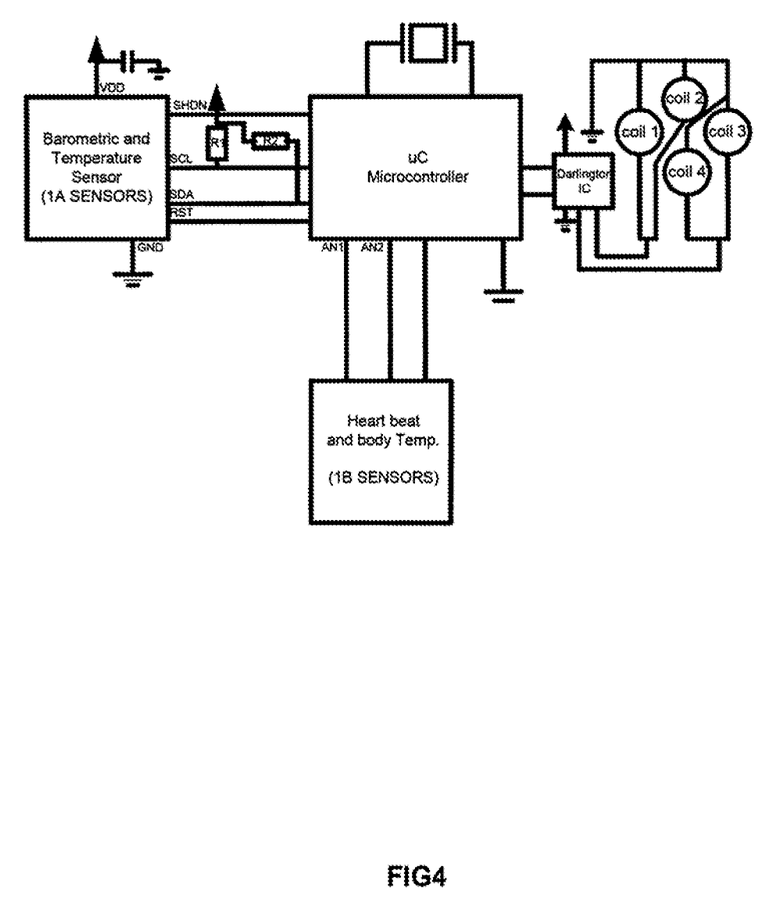
FIG. 4 is an electrical schematic for another embodiment of the disclosure which includes environmental and bodies sensors in communication with a microcontroller and the microcontroller in communication with preferably four coils, though the number of coils is not considered limiting.

FIG. 4 shows another embodiment for the apparatus for regenerating and healing live human and animal bodies by varying the low frequency and intensity of an electromagnetic field in accordance with environmental and body conditions using an algorithm programmed and stored and running thru a microcontroller.

Figure 5:
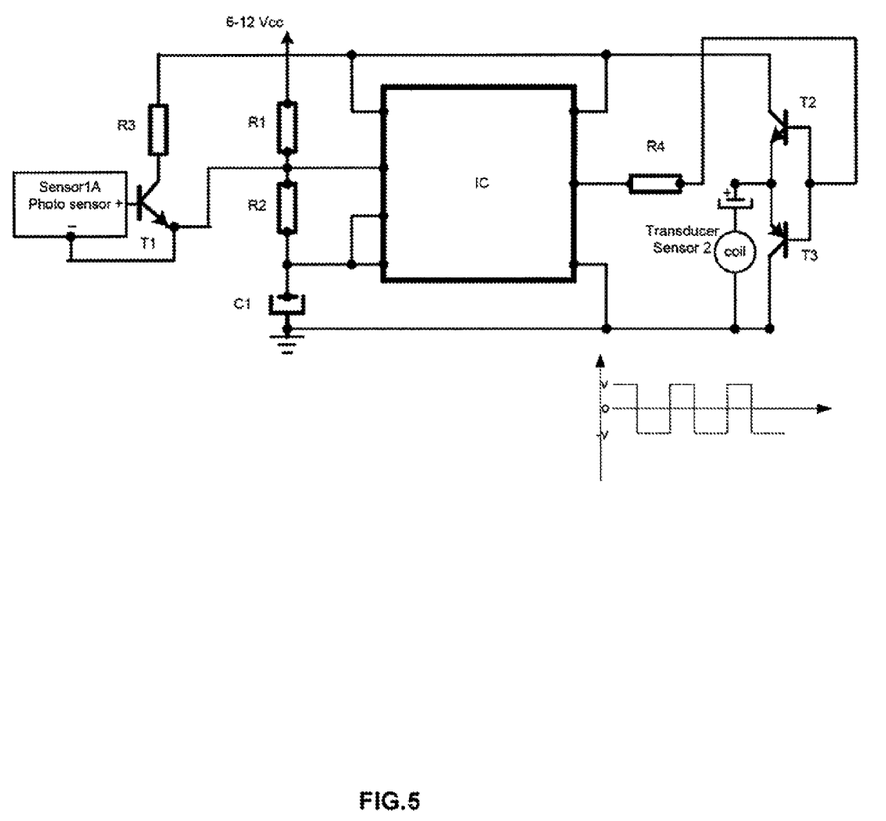
FIG. 5 is an electrical schematic for a further embodiment of the disclosed apparatus using an IC chip and at least one environmental sensor with square wave alternative DC.

FIG. 5 discloses an electrical diagram which produces an alternating DC square wave for its output. Generally, resistors R1 and R2 and capacitor C1 in conjunction with IC chip generate a base frequency. In one embodiment, the IC chip can function as an oscillation circuit. Resistor R3 and transistor T1 can be provided to change, vary or switch the base frequency up or down and also to change the duty cycle which increases or decreases the power of the output accordingly. Resistor R4 can be provided to energize the base of transistors T2 or T3. Transistors T2 and T3 can be provided to amplify the signal received from the IC chip and create differentiation of the DC pulse output, and also determine the polarity of the magnetic field. Other electrical or electronic components that will perform the same functions can be used in replace of any of the above or below described electrical or electronic components. Similar positioned electrical or electronic components shown or described for other embodiments of the apparatus function similar to the functions described in FIG. 5.

Figure 6:
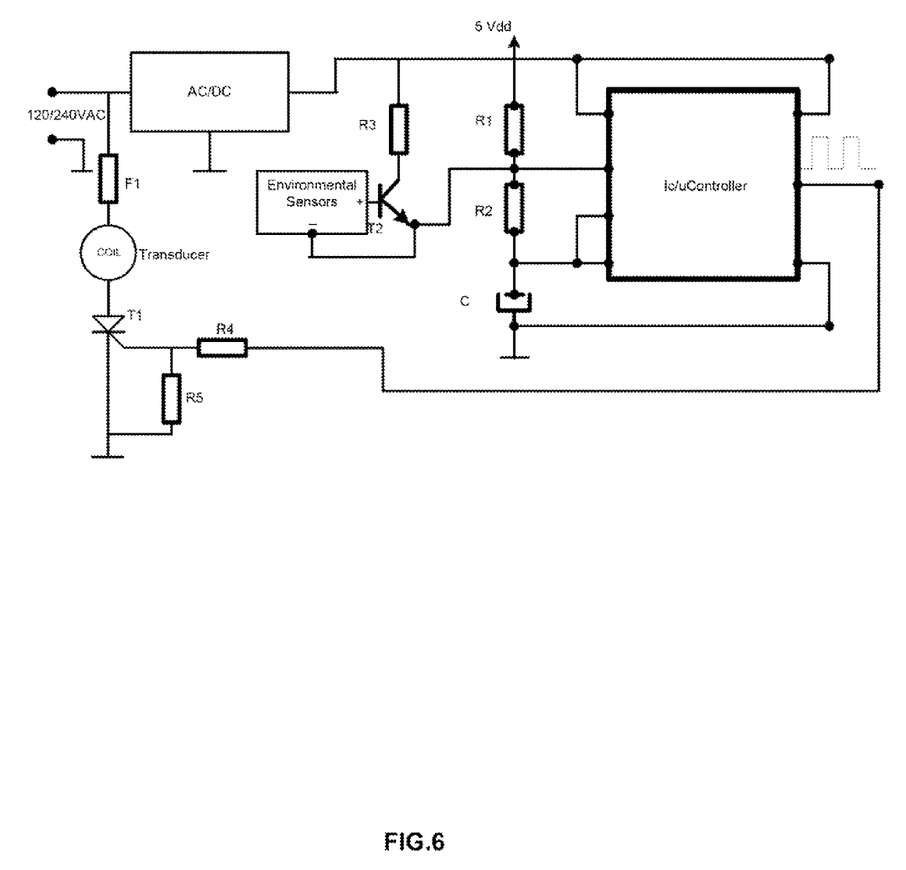
FIG. 6 is an electrical schematic for still another embodiment of the disclosed apparatus preferably using at least one environmental sensor in communication with the an IC microcontroller chip, with the output signal from the microcontroller a gate T1 to allow the coil to be energized by a high voltage AC circuit and generating a magnetic pulse field.

FIG. 6 discloses an electrical schematic showing one or more environmental sensors that can be used to control and determine the cycles for producing magnetic energy, in connection with any type of 120/240 AC outlet. The circuit can be a low voltage AC to DC circuit, which can be made with discrete components or by integrating a AC to DC converter, providing for an output for about 5 V DC for the IC oscillator or microcontroller. The output of the IC or microcontroller will generate train square pulses determined by the environmental sensors. The square pulses can be applied to the gate of TRIAC (T1). Based on the environmental sensors, the signal cycles sent to the gate of TRIAC T1 allows the high voltage to pass through the transducer producing the pulsed magnetic energy and allows the alternating current (with a frequency preferably between about 47 to about 65 Hz) to pass through the transducer at a preferred frequency of about 7 to about 30 Hz as dictated by the sensors.

Figure 7:
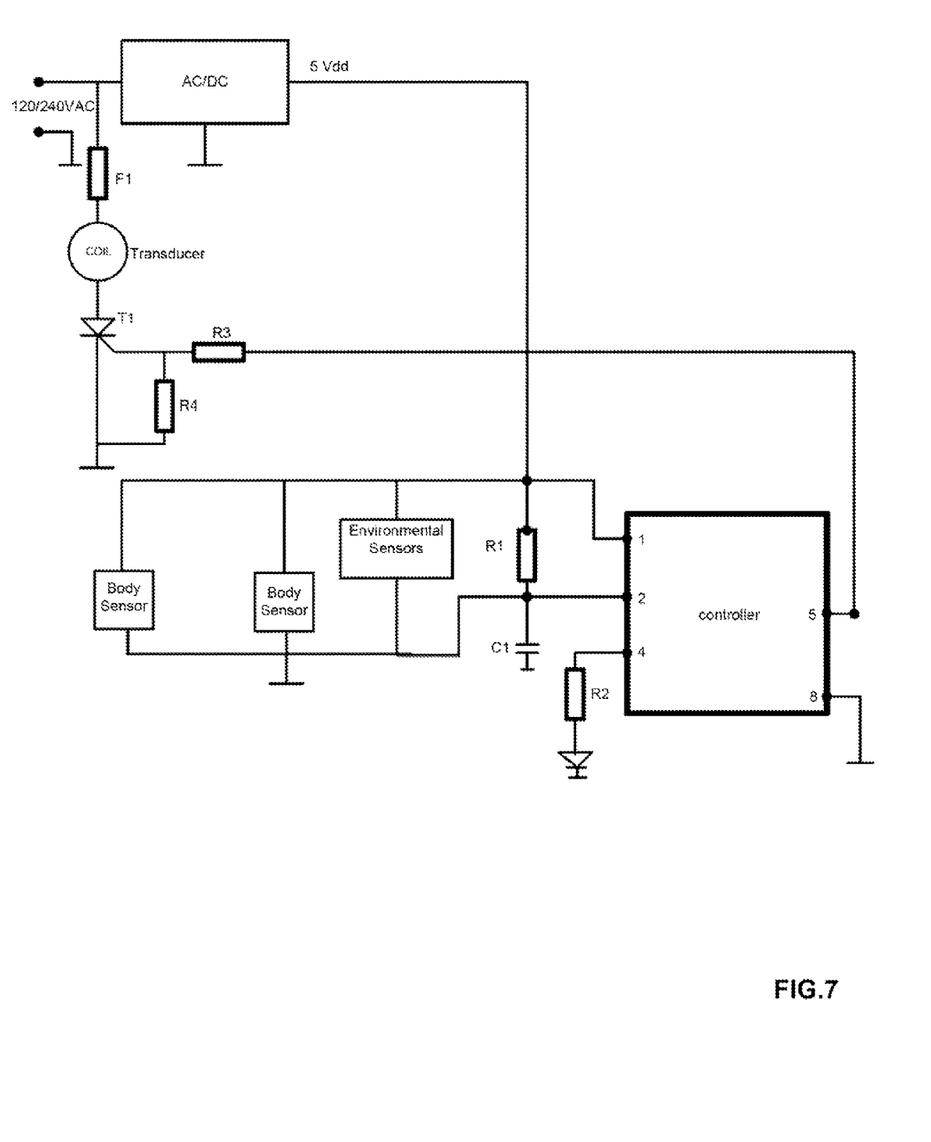
FIG. 7 is an electrical schematic of yet another embodiment of the disclosed apparatus.

FIG. 7 shows a general basic interconnection of environmental and body sensor connected to a microcontroller (non-limiting ex.PIC 12F629). The output of the microcontroller opens the gate of TRIAC T1, producing magnetic force in connection with any 120/240 V ac.

Figure 8:
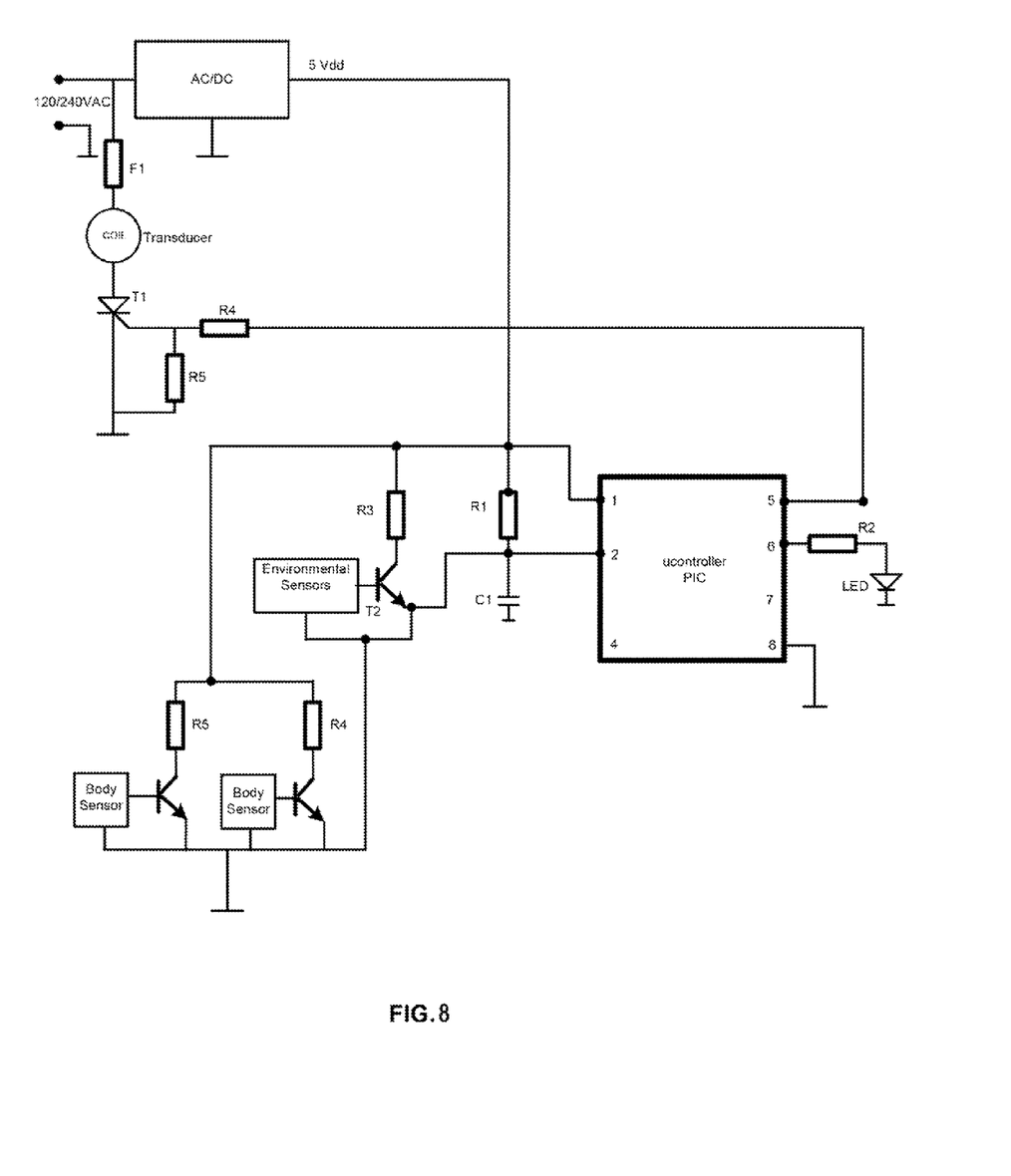
FIG. 8 is an electrical schematic of even still another embodiment of the disclosed apparatus.

In FIG. 8 the magnetic pulse generator uses a microcontroller having a clock frequency set by an external RC. The output frequency can be adjusted by resistor R1. Resistor R1 can be connected in parallel with one or more resistors (R3, R4, and R5) based on the state of the associated sensors. The pulses generated can be equal in length and can open TRIAC T1 allowing the coil to be energized by the AC voltage.

Figure 9:
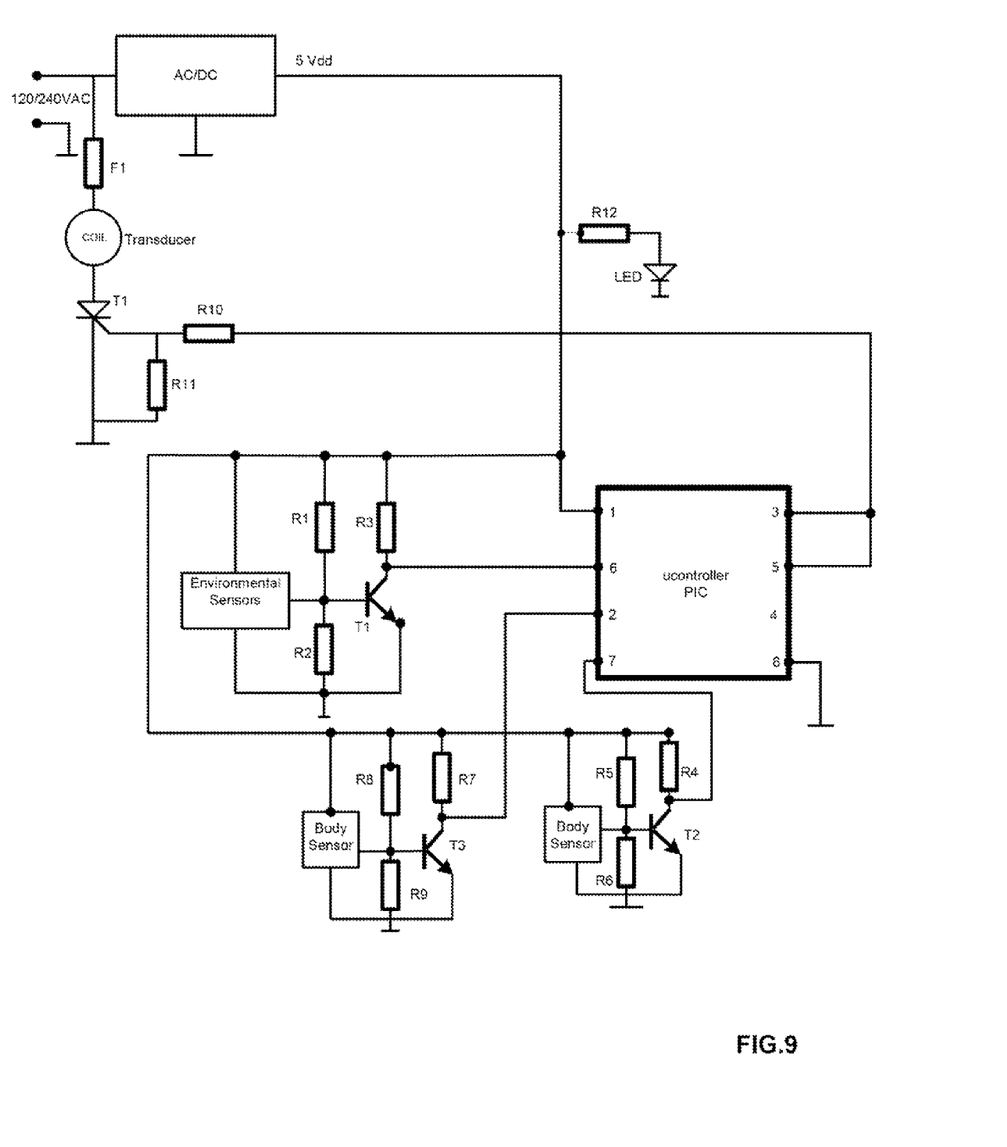
FIG. 9 is an electrical schematic of still further another embodiment of the disclosed apparatus.

In FIG. 9 environmental and body sensor's sensitivity can be adjusted by programming a comparator threshold level in the controller software. Each sensor can produce an electric signal in response to a designated environmental or body purpose (ex. temperature, humidity, heartbeat, pH. etc.). Transistors T2, T3, T4 can be provided to amplify the signals and allows adjustments of the circuit sensitivity by altering the bios voltage of transistors (T2, T3, T4). A short electric pulse from the output of the microcontroller can be sufficient to open the gate of T1 and energize the coil through the alternating voltage.

Figure 10:
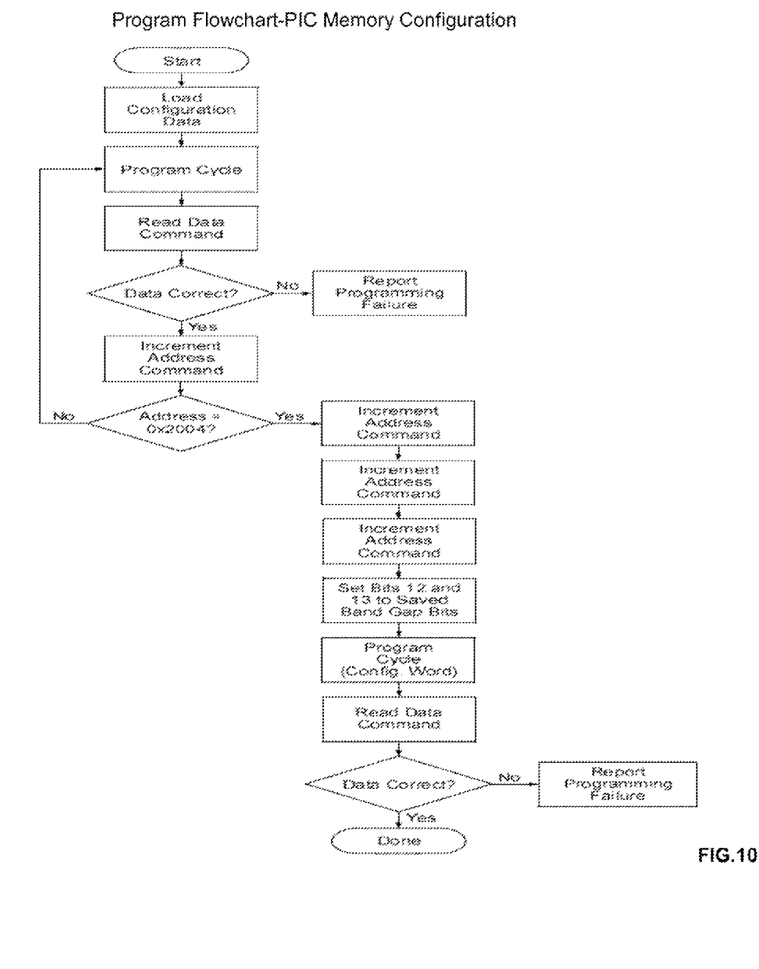
FIG. 10, FIG. 11 and FIG. 12 are flowcharts for the memory configuration, data memory and memory program for the disclosed apparatus.
Figure 11:
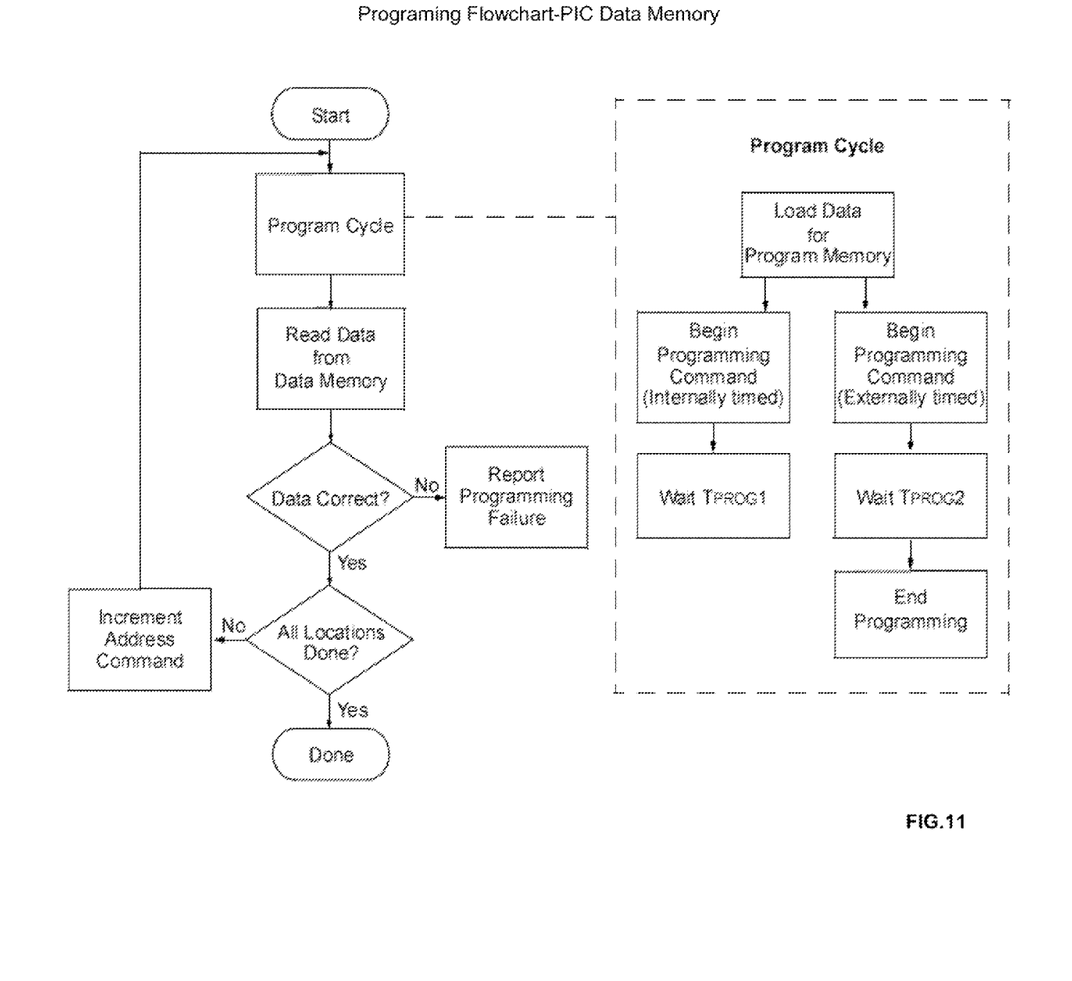
Figure 12:
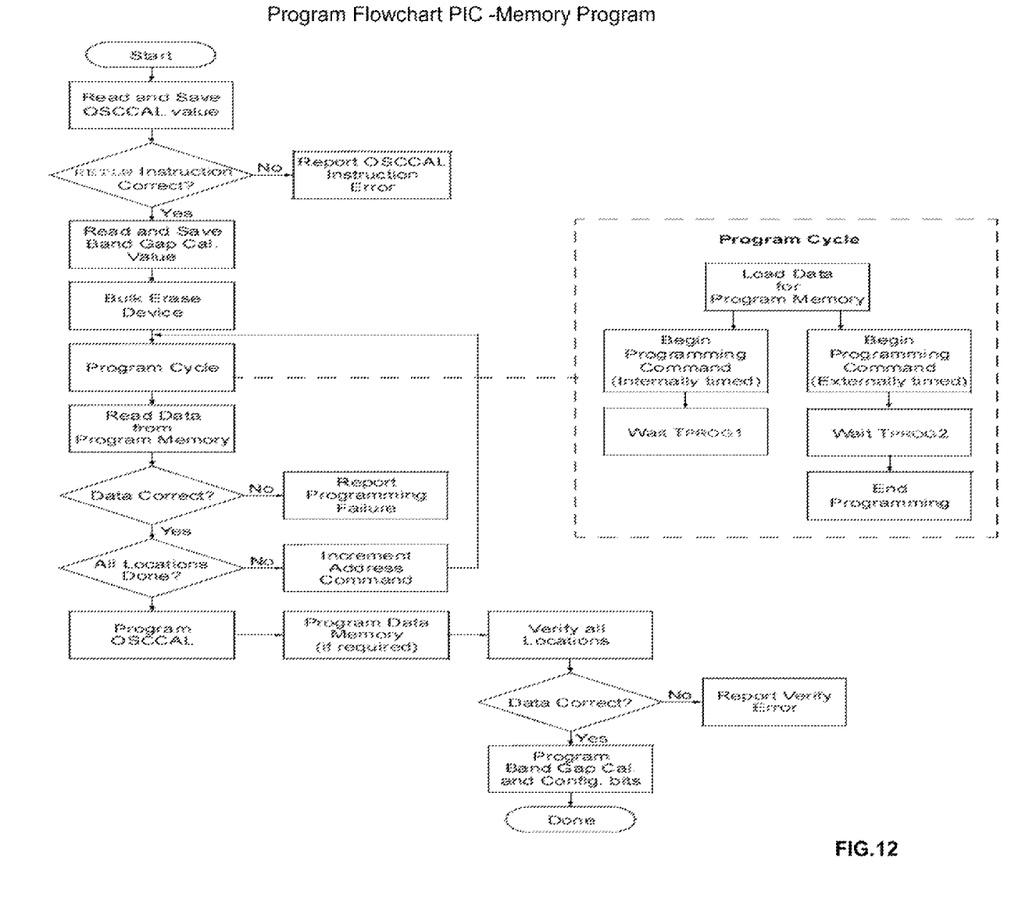

FIG. 10, FIG. 11 and FIG. 12 illustrate the steps and decisions performed in connection with the memory configuration; data memory and memory program, respectively, for the apparatus.

The disclosed apparatus can provide for a magnetic pulse generator, with low frequency using an IC chip or controller to open a gate, whose opening allows high voltage (AC) to energize the transducer (coil) for specific period of time. Preferably, the frequency can be programmed to range anywhere from about 1 Hz to about 170 Hz, though such range is not considered limiting.

In summary, the disclosure provides for a method and apparatus for regenerating and healing a live human or animal body. The apparatus can be comprised of at least one sensor (environmental sensor and/or body sensor); an electrical circuit generating ultra-low frequency DC waves with varying (about 1 to about 30 Hz) based on information received from the sensor(s), and a transducer or electromagnetic resonator creating an electromagnetic force based on the output of the electrical circuit, by opening the gate of a TRIAC, semiconductor device or other electronic device at ultra-low frequency, allowing low frequency AC current to energize the transducer and thus providing for a novel and effective way to rejuvenate (regenerate, heal, balance) live human and animal bodies. The above described apparatus and method can preferably also be comprised with at least one varying component influenced by the information received from the sensor(s); and can produce a low frequency from about 1 Hz to about 30 Hz, preferably provided in a square wave form and can have an electromagnetic force intensity from about 0.001 Gauss to about 0.45 Gauss.

Preferably, the gate (from a TRIAC, other semiconductor device or other electronic device with the equivalent of a gate) can be opened/enabled at an ultra-low frequency provided by the electrical circuit varying the frequency and the duty cycles. With the gate enabled, on the positive side of the duty cycles (which can vary with the frequency based on information from the sensor(s) the transducer can be energized with sinusoidal wave, low frequency AC current from an AC power supply.

The transducer will be energize with short AC sinusoidal waves low frequency (preferably about 47 to about 65 Hz) current (which preferably never start and stop at same phase or point) only on the positive side of duty cycles generated by the ultra-low frequency from the electric circuit, varying the ultra-low frequency, and duty cycle based on information from at least one environmental and/or body sensor. In order to closely replicate earth's magnetic pulse, the AC sinusoidal wave forms preferably do not all start and stop at the same phase or point such that there is no repeating pattern for the starting and stopping phase point.

The body and environmental sensors could be an integral of the device and function as describe above, or the sensors can be separate from the device and communicate with the device using known and future developed wireless communication protocols without changing the functionality described.

In the wireless configuration, the sensors can be a separate module which communicates wirelessly with the main device. Alternatively, the sensors can be existing sensors, such as those provided using an app on an electronic device, such as, but not limited to, a smart phone, cell phone or tablet. In either wireless embodiment, the sensors can communicate with the main device in order to change the variables as describe above. Non-limiting examples of sensor information that can be obtained using software apps for an electronic device include, but are not limited to, heartbeat, body temperature, blood sugar level, etc. The information obtained can be wirelessly sent to the main device and have same functionality and results, benefits, etc. similar to the sensors that are provided as an integral part of the device.

The above described parts can be provided within a housing. Where the sensors are integral, the at least one environmental and/or body sensor, the TRIAC (or other semiconductor or electrical device), the electrical circuit and the transducer or electromagnetic resonator can be contained within the housing. In the above described wireless configuration, the sensors would not be contained within the housing. Additionally, an electrical plug having at least two prongs can extend out of the housing, with the plug connecting the apparatus with a source of high voltage AC when the at least two prongs are inserted within a live electrical socket outlet.

All measurements, amounts, frequencies, voltages, intensity amounts, sizes, shapes, percentages, configurations, securement or attachment mechanisms, dimensions, sealing members, numbers, ranges, part locations, values, percentages, materials, orientations, methods of manufacture, etc. discussed above or shown in the drawing figures are merely by way of example and are not considered limiting and other measurements, amounts, frequencies, voltages, intensity amounts, sizes, shapes, percentages, configurations, securement or attachment mechanisms, dimensions, sealing members, numbers, ranges, part locations, values, percentages, materials, orientations, methods of manufacture, etc. can be chosen and used and all are considered within the scope of the invention.

Furthermore, one or more features, characteristics, sensors, etc. discussed for one embodiment of the disclosure can also be used with another of the above discussed embodiments of the disclosure.

Though the disclosed apparatus is preferably for use with human and mammals, the apparatus can be modified to account for body conditions of other types of living creatures, such as, but not limited to, dogs, horses, cats, reptiles, plants and therefore the concepts, methods and apparatuses of the disclosure are also considered to include use with other types of living creatures.

Additionally, for any numerical ranges discussed above, any combination of numbers within the range can be used to create a smaller size range from the outer limits of the numerical range specified and all such smaller ranges are also considered to be within the scope of the disclosure and also incorporated by reference without particularly listing each specific numerical values for the smaller ranges.

Unless feature(s), part(s), component(s), characteristic(s) or function(s) described in the specification or shown in the drawings for a claim element, claim step or claim term specifically appear in the claim with the claim element, claim step or claim term, then the inventor does not considered such feature(s), part(s), component(s), characteristic(s) or function(s) to be included for the claim element, claim step or claim term in the claim for examination purposes and when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the disclosed apparatus and method have been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. An apparatus for producing a train of electromagnetic pulses, for varying electromagnetic intensity and frequency, and for alternating polarity of the electromagnetic pulses based on information received regarding changes to environmental conditions, said apparatus comprising:
    at least one environmental sensor;
    an electrical component having an electrical gate;
    at least one transducer or electromagnetic resonator in electrical connection with a source of high AC voltage and capable of generating the train of electromagnetic pulses; and
    an electrical circuit producing an output, said output being ultra-low frequency waves having a duty cycle, said electrical circuit in electrical communication with the at least one environmental sensor and the at least one transducer or electromagnetic resonator, said electrical circuit including a microcontroller or IC oscillator chip capable of varying a frequency or an intensity of the electromagnetic pulses, said output of said electrical circuit being sent to and enabling the gate of said electrical component, wherein enabling of the gate occurs only on a positive side of the duty cycle so as to energize the at least one transducer or electromagnetic resonator with short AC sinusoidal wave forms at low frequency AC current from the source of high AC voltage, wherein the short AC sinusoidal wave forms do not share a same phase or starting point such that there is no repeating pattern for a starting and stopping phase point in order to closely replicate earth's magnetic pulse;
    wherein the ultra-low frequency waves of the output are automatically and continuously varied based on information the microcontroller or IC oscillator chip receives from the at least one environmental sensor;
    wherein said at least one transducer or electromagnetic resonator generates said electromagnetic pulses when the output of the electrical circuit enables the gate of the electrical component and wherein the output produced by the electrical circuit is based on a frequency dictated by the at least one environmental sensor;
    wherein a change in the frequency of the output causes changes in the electromagnetic intensity and frequency and in the polarity of the train of electromagnetic pulses created by the at least one transducer or electromagnetic resonator.

2. The apparatus of claim 1 wherein the ultra-low frequency waves of the output of the electrical circuit are ultra-low frequency square wave pulses, wherein values of the square wave pulses are determined by information received from the at least one environmental sensor.

3. The apparatus of claim 1 wherein when the gate of the electrical component is enabled, the low frequency short AC sinusoidal wave forms is permitted to pass through the at least one transducer or electromagnetic resonator to produce the train of electromagnetic pulses.

4. The apparatus of claim 1 wherein said at least one environmental sensor is a photo, temperature, humidity or atmospheric pressure sensor.

5. The apparatus of claim 1 wherein said electrical circuit varies the frequency of the output from between 1 Hz to 30 Hz based on information received from said at least one environmental sensor and the electrical circuit automatically varies the frequency of the output up or down from a starting frequency point; wherein the varying of the frequency of the output automatically causes the electromagnetic intensity to also vary, wherein the low frequency of the short AC sinusoidal wave forms is between about 47 HZ to about 65 Hz.

6. The apparatus of claim 1 wherein said electrical circuit varies the frequency of the output from between 1 Hz to 170 Hz based on information received from said at least one environmental sensor.

7. The apparatus of claim 1 wherein said electromagnetic intensity created by said at least one transducer or electromagnetic resonator is between 0.001 Gauss to 0.45 Gauss.

8. The apparatus of claim 1 wherein said output is in an AC pulse sinusoidal wave form.

9. The apparatus of claim 1 further comprising at least one body condition sensor in electrical communication with the electrical circuit.

10. The apparatus of claim 1 wherein the source of high voltage is 120 VAC or 240 VAC.

11. The apparatus of claim 1 wherein said at least one environmental sensor is a combined barometric pressure and temperature sensor.

12. The apparatus of claim 1 wherein said source of high AC voltage is a 120/240 AC outlet, wherein when the apparatus is connected to the outlet, the gate of the electrical component allows high voltage AC current to energize the at least one transducer or electromagnetic resonator for specific periods of time.

13. An apparatus for producing a train of electromagnetic pulses, for varying electromagnetic intensity and frequency, and for alternating polarity of the electromagnetic pulses based on information received regarding changes to environmental conditions, said apparatus comprising:
    at least one environmental sensor comprising a combined barometric pressure and temperature sensor:
    a TRIAC having a gate;
    at least one transducer or electromagnetic resonator in electrical connection with a source of high AC voltage and capable of generating the train of electromagnetic pulses; and
    an electrical circuit producing an output, said output being ultra-low frequency waves having a duty cycle which is automatically and continuously varied by the electrical circuit based on information received from the at least one environmental sensor, said electrical circuit in electrical communication with the at least one environmental sensor and the at least one transducer or electromagnetic resonator, said electrical circuit including a microcontroller or IC oscillator chip capable of varying a frequency or an intensity of the electromagnetic pulses, said output of said electrical circuit being sent to and enabling the gate of the TRIAC, wherein enabling of the gate occurs only on a positive side of the duty cycle so as to energize the at least one transducer or electromagnetic resonator with short AC sinusoidal wave forms at low frequency AC current from the source of high AC voltage, wherein the short AC sinusoidal wave forms do not share a same phase or starting point such that there is no repeating pattern for a starting and stopping phase point in order to closely replicate earth's magnetic pulse;

wherein said at least one transducer or electromagnetic resonator generates said electromagnetic pulses when the output of the electrical circuit enables the gate of the TRIAC and wherein the output produced by the electrical circuit is based on a frequency dictated by the at least one environmental sensor;

wherein the output of the electrical circuit are square wave pulses that are determined by the at least one environmental sensor;

wherein said electrical circuit varies the frequency of the output from between 1 Hz to 170 Hz based on information received from said at least one environmental sensor;

wherein said electromagnetic intensity created by said at least one transducer or electromagnetic resonator is between 0.001 Gauss to 0.45 Gauss;

wherein a change in the frequency of the output causes changes in the electromagnetic intensity and frequency and in the polarity of the train of electromagnetic pulses created by the at least one transducer or electromagnetic resonator wherein said source of high AC voltage is an 120/240 AC outlet, wherein when the apparatus is connected to the outlet the gate of the TRIAC allows high voltage AC current to energize the at least one transducer or electromagnetic resonator for specific periods of time.

14. The apparatus of claim 13 wherein said at least one environmental sensor also comprises a photo sensor.

15. The apparatus of claim 13 further comprising at least one body condition sensor in electrical communication with the electrical circuit.

16. The apparatus of claim 13 wherein the at least one environmental sensor is in wireless communication with the electrical circuit, wherein the at least one environmental sensor is disposed in a separate module or separate electronic device from the electrical circuit.

17. The apparatus of claim 13 further comprising a housing wherein the at least one environmental sensor, the TRIAC, the electrical circuit and the at least one transducer or electromagnetic resonator are contained within the housing to form an integral device.

18. The apparatus of claim 17 further comprising an electrical plug having at least two prongs extending out of said housing, said plug connecting the apparatus with the source of high AC voltage when the at least two prongs are inserted within the outlet.

* * * * *